United States Patent
Minko et al.

(10) Patent No.: US 11,896,713 B2
(45) Date of Patent: Feb. 13, 2024

(54) STRATEGIES TO ENHANCE LUNG CANCER TREATMENT

(71) Applicant: Rutgers, The State University of New Jersey, New Brunswick, NJ (US)

(72) Inventors: Tamara Minko, East Brunswick, NJ (US); Olga B. Garbuzenko, Skillman, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 17/508,535

(22) Filed: Oct. 22, 2021

(65) Prior Publication Data

US 2022/0125728 A1   Apr. 28, 2022

Related U.S. Application Data

(60) Provisional application No. 63/104,131, filed on Oct. 22, 2020.

(51) Int. Cl.
*A61K 9/127* (2006.01)
*A61K 9/00* (2006.01)
(Continued)

(52) U.S. Cl.
CPC .......... *A61K 9/1272* (2013.01); *A61K 9/0078* (2013.01); *A61K 31/277* (2013.01); *A61K 31/282* (2013.01); *A61K 31/337* (2013.01); *A61K 31/365* (2013.01); *A61K 31/506* (2013.01); *A61K 31/517* (2013.01); *A61K 31/5377* (2013.01); *A61K 31/553* (2013.01); *A61K 31/704* (2013.01);
(Continued)

(58) Field of Classification Search
CPC .. A61K 9/1272; A61K 9/0078; A61K 31/277; A61K 31/282; A61K 31/337; A61K 31/365; A61K 31/506; A61K 31/517; A61K 31/5377; A61K 31/553; A61K 31/704; A61K 33/243; A61K 47/64; A61K 9/127; A61K 9/5123; A61P 35/00
See application file for complete search history.

(56) References Cited

U.S. PATENT DOCUMENTS 9,040,585 B2 *   5/2015   Degterev ................ A61P 35/00
                                                               435/375
2008/0008662 A1 *   1/2008   Knight .................... A61P 11/00
                                                               424/45
(Continued)

FOREIGN PATENT DOCUMENTS

CA           2878152        *   1/2014
CA          2 896 571       *  11/2017
WO    WO-9422429 A1 *  10/1994   ....... A61K 47/48815

OTHER PUBLICATIONS

Saad, et al: "Receptor Targeted Polymers, Dendrimers, Liposomes: Which Nanocarrier is the Most Efficient for Tumor-Specific Treatment and Imaging?", J Control Release, Sep. 10, 2008, 130(2): 107-114. doi:10.1016/j.jconrel.2008.05.024.

Garbuzenko et al: "Inhalation Treatment of Lung Cancer: The Influence of Composition, Size and Shape of Nanocarriers on their Lung Accumulation and Retention", Cancer Biol Med, 2014;11:44-55. doi; 10.7497/j.issn.2095-3941.2014.01.004.

(Continued)

*Primary Examiner* — Gollamudi S Kishore
(74) *Attorney, Agent, or Firm* — Fox Rothschild LLP

(57) ABSTRACT

A nanocarrier containing a combination of bioactive agents is provided. The nanocarrier allows for targeted delivery of the agents to cancer cells with minimized side effect.

17 Claims, 1 Drawing Sheet

Specification includes a Sequence Listing.

Nanostructured Lipid Carriers siRNA     Paclitaxel     LHRH Peptide     PEG

(51) Int. Cl.
*A61K 31/337* (2006.01)
*A61K 31/282* (2006.01)
*A61K 33/243* (2019.01)
*A61K 31/704* (2006.01)
*A61P 35/00* (2006.01)
*A61K 31/5377* (2006.01)
*A61K 31/506* (2006.01)
*A61K 31/553* (2006.01)
*A61K 31/365* (2006.01)
*A61K 31/277* (2006.01)
*A61K 47/64* (2017.01)
*A61K 31/517* (2006.01)

(52) U.S. Cl.
CPC ............ *A61K 33/243* (2019.01); *A61K 47/64* (2017.08); *A61P 35/00* (2018.01)

(56) References Cited

U.S. PATENT DOCUMENTS

| | | | | |
|---|---|---|---|---|
| 2009/0074852 A1* | 3/2009 | Kaufmann | ............ | A61P 35/04 435/375 |
| 2010/0008978 A1* | 1/2010 | Drummond | ............ | A61K 31/00 514/44 A |
| 2015/0071988 A1* | 3/2015 | Konduri | ............ | A61K 31/7032 424/94.64 |

OTHER PUBLICATIONS

Dharap et al: "Tumor-Specific Targeting of an Anticancer Drug Delivery System by LHRH Peptide", PNAS, Sep. 6, 2005, vol. 102, No. 36, pp. 12962-12967.

* cited by examiner

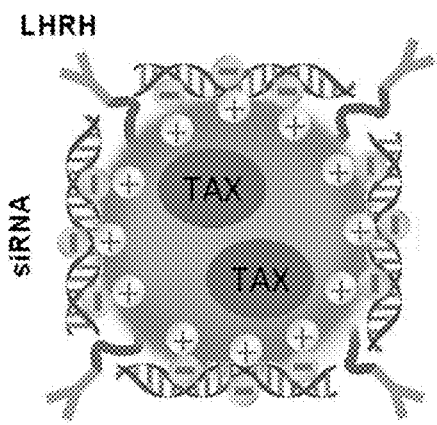
Nanostructured Lipid Carriers
 siRNA  Paclitaxel ⟫ LHRH Peptide ⋀ PEG

SEQUENCE LISTING

```
<160> NUMBER OF SEQ ID NOS: 19

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
cugaguuuaa aaggcaccct t                                           21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcagtcttat ctaactatga t                                           21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gaagaagtgt ccccgtaatt a                                           21

<210> SEQ ID NO 4
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gaggtcagtc accctaaaca a                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gacaatgata cagctacata a                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatttcatat gcacgtacat t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gataacagat ggacatacta t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gattgtgcat acagactagt t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gaaacaatga aggatgatag a                                              21

<210> SEQ ID NO 10
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 10

Gln Trp Ala Val Gly His Leu Leu
1               5

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Phe Phe Tyr Gly Gly Ser Arg Gly Lys Arg Asn Asn Phe Lys Thr
1               5                   10                  15

Glu Glu Tyr

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Asp Cys Arg Gly Asp Cys Phe Cys
1               5

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Arg Lys Lys Arg Arg Gln Arg Arg Arg Pro Pro Gln
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Gln Ile Lys Ile Trp Phe Gln Asn Arg Arg Met Lys Trp Lys Lys
1               5                   10                  15

<210> SEQ ID NO 15
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15
```

```
Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
                20                  25                  30

Glu Gly Thr
        35

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Leu Ala Gly Leu Ala Gly Leu Leu Gly Leu Glu Gly Leu Leu Gly
1               5                   10                  15

Leu Pro Leu Gly Leu Leu Glu Gly Leu Trp Leu Gly Leu Glu Leu Glu
                20                  25                  30

Gly Asn

<210> SEQ ID NO 17
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Gly Gly Asp Gly Gly Asp Gly Gly Asp Gly Pro Leu Gly Leu Ala
1               5                   10                  15

Gly Arg Arg Arg Arg Arg Arg Arg Arg Cys
                20                  25

<210> SEQ ID NO 18
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Ile Ala Ser His Leu Leu Ala Tyr Phe Phe Thr Glu Leu Asn Gly
1               5                   10                  15

Lys Pro Ile Leu Phe Phe
                20

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Arg Glu Ala
1
```

STRATEGIES TO ENHANCE LUNG CANCER TREATMENT

CROSS-REFERENCE TO RELATED APPLICATIONS

This application claims priority under 35 U.S.C. 119(e) to U.S. Provisional Patent Application Ser. No. 63/104,131, filed on Oct. 22, 2020, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Dec. 20, 2021, is named 070439 01654 SL.txt and is 5,595 bytes in size.

STATEMENT REGARDING FEDERALLY SPONSORED RESEARCH OR DEVELOPMENT

This invention was made with government support under Grant No. R01 CA238871 awarded by the National Institutes of Health and National Cancer Institute. The government has certain rights in the invention.

TECHNICAL FIELD

Disclosed herein is a nanoparticle-based complex to target cancer cells using target-directed ligand incorporated with liposomes, nanostructured lipid carriers (NLS), pool of siRNAs and anticancer agent for targeted delivery.

BACKGROUND

Non-Small Cell Lung Carcinoma (NSCLC), is the most common type of lung cancer (more than 80% of all cases). The majority of NSCLC patients are diagnosed in the advanced or metastatic stage of the disease, when treatment options are limited to surgery, chemotherapy, few targeted- and immunotherapy. Small molecule Tyrosine Kinase (TK) Inhibitors acting on the Epidermal Growth Factor Receptors (EGFRs) are standard therapies for patients with NSCLC harboring EGFR-TK inhibitor-sensitizing mutations. However, fewer than 10% of patients with NSCLC benefit from this therapy. Moreover, even the latest generation of EGFR inhibitors can cause severe systemic toxicities and are ineffective in preventing non-canonical EGFR signaling.

Consequently, the development of additional effective and safe approaches to treat this disease is vitally important. However, limited clinical efficiency, toxicity and development of resistance represent three critical barriers diminishing progress in the therapy of NSCLC. There is a need for developing new approaches to cancer treatment.

SUMMARY

This patent document discloses a novel nanocarrier system for delivering a combination of therapeutic agents for cancer treatment. The advantage of the delivery approach includes: suppression of all four types of EGFR-TKs by a pool of small interfering RNAs (siRNAs); induction of cell death by an anticancer drug, enhancing the efficiency of the treatment by the local inhalation delivery of therapeutic agents directly to the diseased organ or tissue such as lung (passive targeting), active receptor-mediated targeting of the therapy specifically to cancer cells that in turn should minimize adverse side effects of treatment, and increased stability, solubility, and cellular penetration of siRNA and drug by using tumor targeted nanocarrier.

An aspect of this document provides a nanocarrier system formulated for in vivo delivery of plurality of bioactive agents by inhalation, comprising:
(a) a lipid-based nanoparticle;
(b) one or more anticancer agents enclosed in the lipid-based nanoparticle;
(c) optionally one, two or more siRNAs distributed on the surface of the nanoparticle;
(d) a first group of polyethylene glycols (PEGs) extending from the surface of the nanoparticle, wherein the PEGs each have an inner terminus bonded to an anchor lipid in the nanoparticle and an outer terminus; and
(e) a ligand bonded to the outer terminus of the PEGs, wherein the ligand is specific to receptors overexpressed in cancer cells.

In some embodiments, the nanoparticle is a liposome. In some embodiments, the nanoparticle comprises two or more lipids selected from the group consisting of triglycerides, partial glycerides, fatty acids, and steroids and waxes. In some embodiments, the nanoparticle is a liposome. In some embodiments, the nanoparticle has an average diameter ranging from about 100 to about 300 nm.

In some embodiments, the anticancer agent is selected from cisplatin, carboplatin, paclitaxel, doxorubicin, erlotinib, gefitinib, afatinib, dacomitinib, osimertinib imatinib, PD 153035, picropodophyllin, PP2, staurosporine, and Tyrphostin AG 490. In some embodiments, the anticancer agent is selected from cisplatin or carboplatin.

In some embodiments, the first group of PEGs has a molecular weight ranging from about 1000 to about 3000 daltons. In some embodiments, the nanoparticle further includes a second group of PEGs extending from the surface of the nanoparticle, wherein the second group of PEGs are not bonded to the ligand.

In some embodiments, the anchor lipid is selected from the group consisting of 1,2-Distearoyl-sn-glycero-3-phosphoethanolamine (DSPE), N[1-(2,3-Dioleoyloxy)propyl]-N,N,N-trimethylammonium methyl-sulfate (DOTAP), and dioleoylphosphatidylethanolamine (DOPE).

In some embodiments, the ligand is Gln-His-Trp-Ser-Tyr-DLys(D-Cys)-Leu-Arg-Pro.

In some embodiments, the nanoparticle further comprises one or more siRNAs distributed on the surface of the nanoparticle. In some embodiments, the siRNAs target one or more of EGFR1, EGFR2, EGFR3, and EGFR4.

Another related aspect of this document provides a kit incorporating the nanocarrier disclosed herein. In some embodiments, the kit is a sprayer or a nebulizer.

A further aspect provides a method of treating cancer comprising administering the nanocarrier disclosed herein by inhalation. The nanocarrier system can be sprayed in aerosol form to a subject in need thereof. In some embodiments, the cancer is lung cancer, which can be non-small cell lung cancer or small cell lung cancer.

DESCRIPTION OF DRAWINGS

FIG. 1 shows an example of a nanostructured lipid carrier.

DETAILED DESCRIPTIONS

Various embodiments of this patent document disclose a nanocarrier system containing a therapeutic agent or a combination of therapeutic agents, which provide an innovative multi-tier approach in cancer treatment. This approach includes inhibition of an entire pool of tyrosine kinases (TKs) in cancer cells by genotherapy with multiple siRNAs combined with chemotherapy. The multifunctional nanocarrier system containing siRNAs and one or more anticancer agents can be delivered directly to target organs (e.g. lungs) to limit adverse side effects of such combinatorial geno- and chemotherapy. To further protect non-cancerous cells and target not only the primary tumor but also possible metastases, an entire system will contain a ligand (e.g. LHRH peptide) specific to extracellular receptors overexpressed in cancer cells. The application of such tumor-targeted, multifunctional approach can substantially enhance the efficiency of the treatment and limit adverse side effects of chemotherapy by simultaneous local delivery (by inhalation to lung) and specific to cancer cells targeted therapy. As a result, suppression of cancer cell proliferation can be achieved as well as limitation of drug resistance, invasion, and metastasis by inhibition of EGFR-TK signaling pathways in combination with chemotherapy.

While the following text may reference or exemplify specific embodiments of a compound, a kit or a method relating to the treatment or prevention of a disease, it is not intended to limit the scope of the compound, kit or method to such particular reference or examples. Various modifications may be made by those skilled in the art, in view of practical and economic considerations, such as the specific salt form of the compound and the amount or frequency of administration of the therapeutic compound for treating or preventing a disease or condition.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "pharmaceutical composition" refers to a mixture of a compound disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. In some embodiments, pharmaceutically acceptable salts of the compounds disclosed herein are provided.

The term "subject" encompasses any animal, but preferably a mammal, e.g., human, non-human primate, a dog, a cat, a horse, a cow, or a rodent. More preferably, the subject is a human.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

The term "pharmaceutically acceptable carrier" refers to a chemical compound that facilitates the delivery or incorporation of a compound or therapeutic agent into cells or tissues.

The term "therapeutically effective amount" or "effective amount" refers to an amount of a compound or composition effective to prevent, alleviate or ameliorate symptoms of disease, prolong the survival of the subject being treated, or reach a desirable/acceptable medical or sanitary condition. Determination of a therapeutically effective amount or effective amount is well within the capability of those skilled in the art, especially in light of the detailed disclosure provided herein.

The term "treating" or "treatment" of any disease or condition refers, in some embodiments, to ameliorating the disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to modulating the disease or disorder, either physically, (e.g., stabilization of a discernible symptom), physiologically, (e.g., stabilization of a physical parameter), or both. In some embodiments, "treating" or "treatment" refers to delaying the onset of the disease or disorder, or even preventing the same. "Prophylactic treatment" is to be construed as any mode of treatment that is used to prevent progression of the disease or is used for precautionary purpose for persons at risk of developing the condition.

In conventional cancer treatment, for example, activation of EGF receptors (EGFR1, EGFR2, EGFR3, EGFR4) in response to ligands (e.g., EGF, TGFα, and others) triggers several downstream signaling pathways via three main signaling branches: Rat Sarcoma (RAS), Phosphatidylinositol 3'-kinase (PI3K) and Signal Transducers and Activators of Transcription (STAT). For instance, three major nonsurgical approaches are currently being used to treat NSCLC: (1) chemotherapy plus immunotherap; (2) monoclonal antibodies (mAb) specific to EGFR blocking EGF signaling pathway and (3) inhibition of EGFR-TK by small-molecule(s). The major disadvantages of chemotherapy by cytotoxic drugs include severe adverse side effects on healthy tissues and development of drug resistance. The disadvantages of EGFR-targeted therapy both by mAb and small-molecule TK inhibitors include: (1) specificity to only a single type of EGFR-TK (and therefore effectiveness only in small fraction of patients) and/or (2) side effects of treatment. The multiplier treatment approach of this patent document overcome these limitations, enhance the efficiency of cancer treatment, and prevent systemic toxicity. This approach includes inhibition of an entire pool of TKs in NSCLC cells by genotherapy with multiple siRNAs combined with chemotherapy. To limit adverse side effects of such combinatorial geno- and chemotherapy, siRNAs and an anticancer drug are combined in one multifunctional nanocarrier system for drug delivery. An example of nanostructrured lipid carrier is shown in FIG. 1.

The nanocarrier system containing active payloads (siRNA and anticancer agent) with dual passive and active targeting approaches (e.g. local delivery by inhalation and targeting specifically to lung cancer cells) allows for a delivery of the highly toxic active components specifically to the tissue or organ with tumor and limiting their accumulation (and possible adverse side effects) in non-tumorous tissues and other healthy organs. A synergistic effect can be achieved in comparison with treatment from individual agents.

The nanocarrier system of NLC incorporates positive characteristics of several different drug carriers used for siRNA and drug delivery including liposomes, solid lipid nanoparticles, polymeric nanoparticles and emulsions. For example, NLC as carriers provide the following advantages when compared with other lipid carriers: (1) improved stability of encapsulated drugs; (2) controlled and/or targeted drug release; (3) high and enhanced content of payload(s); (4) ability to carry both drugs and nucleic acids; (5) ability to incorporate tumor-specific targeting ligand; (6) excellent biocompatibility (composed of biodegradable lipids); (7) easy sterilization and scale-up production for animal experiments and clinical trials; (8) water-based technology (avoiding potentially toxic organic solvents); and (9) less expensive than polymeric/surfactant based carriers.

An aspect of this document provides a nanocarrier system formulated for in vivo delivery of plurality of bioactive agents by inhalation, comprising:

(a) a lipid-based nanoparticle;

(b) an anticancer agent enclosed in the lipid-based nanoparticle;

(c) optionally one, two or more siRNAs distributed on the surface of the nanoparticle;

(d) a first group of polyethylene glycols (PEGs) extending from the surface of the nanoparticle, wherein the PEGs each have an inner terminus bonded to an anchor lipid in the nanoparticle and an outer terminus; and (e) a ligand bonded to the outer terminus of the PEGs, wherein the ligand is specific to receptors overexpressed in cancer cells.

In some embodiments, the nanoparticle is prepared from two or more lipids. Nonlimiting examples of the lipids include triglycerides (e.g. tri-stearin), partial glycerides (e.g. monoglycerides (two hydroxyl groups free) or diglycerides (one hydroxyl group free)), fatty acids (e.g. stearic acid, palmitic acid), and steroids (e.g. cholesterol) and waxes (e.g. cetyl palmitate). In some embodiments, at least one of the lipids is a solid and at least one of the lipids is a liquid at room temperature. This mixing will result in a less ordered lipid matrix with many imperfections that help to accommodate a higher amount of payload. The ratio between the solid lipid and the liquid lipid can range from about 1:5 to about 5:1, or from about 1:2 to about 2:1. In some embodiments, the nanoparticle further comprises a positively charge lipid.

In some embodiments, the nanoparticle has an average diameter ranging from about 50 to about 800, from about 50 to about 500, from about 50 to about 300, from about 100 to about 300, from about 100 to about 200, or from about 100 to about 150 nm. Nonlimiting examples of the diameter include about 50, about 80, about 100, about 120, about 150, about 180, about 200, about 250, about 300, about 350, about 400, about 450, about 500, and about 600 nm.

Various small-molecule anticancer agents can be incorporated into the nanoparticle. In some embodiments, the anticancer agent is physically encapsulated or entrapped in the nanoparticle without forming covalent bonds with the nanoparticle. Nonlimiting examples include TK inhibitors (lapatinib, afatinib, dacomitinib, osimertinib, ibrutinib, nazartinib, beratinib erlotinib, or gefitinib). Additional examples of inhibitors include imatinib, PD 153035, picropodophyllin, PP2, staurosporine, and Tyrphostin AG 490.

In some embodiments, the anticancer gent is mTOR inhibitor. Nonlimiting examples of the mTOR inhibitor include rapamycin, temsirolimus, everolimus, and ridaforolimus.

The pool of siRNAs in the nanocarrier may target two, three or four of EGFR1, EGFR2, EGFR3, and EGFR4. In some embodiments, the siRNAs in combination target all four EGFR receptors. Nonlimiting exampels of siRNAs include SMARTpool: siGENOME EGFR siRNA-M-003114-03-0050 (Dharmacon). Additional examples of siRNA are those disclosed in WO2009079790, the entire disclosure of which is hereby incorporated by reference. The siRNA can bind to the lipid nanoparticle via a cationic agent or lipid or bind to an outer lipid surface of the lipid nanoparticle via a disulfide bond. In some embodiments, the pool of negatively charged (in physiological pH) siRNA are conjugated to the positively charged lipid membrane of cationic liposome at the surface.

In some embodiments, the pool of siRNAs include one, two, three or four of the following:

```
                         (SEQ ID NO: 1)
CUGAGUUUAAAAGGCACCCTT (SEQ ID NO: 2)
GCAGTCTTATCTAACTATGAT (SEQ ID NO: 3)
GAAGAAGTGTCCCCGTAATTA (SEQ ID NO: 4)
GAGGTCAGTCACCCTAAACAA (SEQ ID NO: 5)
GACAATGATACAGCTACATAA (SEQ ID NO: 6)
GATTTCATATGCACGTACATT (SEQ ID NO: 7)
GATAACAGATGGACATACTAT (SEQ ID NO: 8)
GATTGTGCATACAGACTAGTT (SEQ ID NO: 9)
GAAACAATGAAGGATGATAGA
```

The loading of the siRNA in the nanocarrier ranges from about 1 to about 4, about 1.5 to about 3, about 1.5 to about 2.5, or about 2 to about 2.5 nmole/mg.

The PEG component serves to attach a target-directed ligand to the nanoparticle as well as modulating the overall properties of the nanoparticle. In some embodiments, the PEGs for attaching the ligand have a molecular weight ranging from about 1000 to about 4000 daltons, from about 1000 to about 3000 daltons, from about 1500 to about 2500 daltons, or from about 1800 to about 2200 daltons. Besides PEG, other biocompatible polymers can also be used to achieve the desired results. Nonlimiting examples of suitable polymers include polypropylene glycol, glycolpoly (lactic acid), poly(lactic-co-glycolic acid), poly(caprolactone), poly(vinyl alcohol), polyurethenes, polyamides and poly(2-hydroxyethyl methacrylate), chitosan, collagen, gelatin, hyaluronic acid, chondroitin sulfates, fibrin, alginate, agarose and cellulose. The polymers can be straight or branched.

While one terminus of the PEG is attached to the ligand, the other terminus of PEG is linked to an anchor lipid, which is mixed with the other lipid components in the nanoparticle. Nonlimiting examples of the anchor lipid include 1,2-Distearoyl-sn-glycero-3-phosphoethanolamine (DSPE), N-[1-(2,3-Dioleoyloxy)propyl]-N,N,N-trimethylammonium methyl-sulfate (DOTAP), and dioleoylphosphatidylethanolamine (DOPE). The attachment of the PEG to the anchor lipid and/or the ligand can be readily accomplished with routine chemistry such as coupling reactions optionally with an activating agent.

Examples of suitable phospholipids include esters of glycerol with one or preferably two (equal or different) residues of fatty adds and with phosphoric acid, wherein the phosphoric acid residue is in turn bound to a hydrophilic group, such as, for example, choline (phosphatidylcholines- PC), serine (phosphatidylserines-PS), glycerol (phosphatidylglycerols-PG), ethanolamine (phosphatidylethanolamines-PE), inositol (phosphatidylinositol). Esters of phospholipids with only one residue of fatty acid are generally referred to in the art as the "lyso" forms of the phospholipid or "lysophospholipids".

Fatty acid residues present in the phospholipids are in general long chain aliphatic acids, typically containing from 12 to 24 carbon atoms, preferably from 14 to 22; the aliphatic chain may contain one or more unsaturated portions or is preferably completely saturated. As used herein, the term "phospholipids" includes either naturally occurring, semisynthetic or synthetically prepared products that can be employed either singularly or as mixtures. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic add are employed.

Further examples of phospholipids are phosphatidic acids (e.g. the diesters of glycerol-phosphoric acid with fatty acids); sphingolipids, such as sphingomyelins (e.g. those phosphatidylcholine analogs where the residue of glycerol diester with fatty acids is replaced by a ceramide chain); cardiolipins (e.g. the esters of 1,3-diphosphatidylglycerol with a fatty acid); glycolipids, such as gangliosides GM1 (or GM2) or cerebrosides; glucolipids; sulfatides and glycosphingolipids. Examples of naturally occurring phospholipids include natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acid di-esters of phosphatidylcholine, ethylphosphatidylcholine, phosphatidylglycerol, phosphatidic acid, phosphatidylethanolamine, phosphatidylserine, and sphingomyelin. Examples of preferred phosphorlipids include, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2-Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-steparoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroylphosphatidylglycerol (DLPG) and its alkali metal salts, diarachidoylphosphatidylglycerol (DAPG) and its alkali metal salts, dimyristoylphosphatidylglycerol (DMPG) and its alkali metal salts, dipalmitoylphosphatidyl-glycerol (DPPG) and its alkali metal salts, distearoylphosphatidylglycerol (DSPG) and its alkali metal salts, dioleoylphosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoylphosphatidylethanolamine (DMPE), dipalmitoylphospha-tidylethanolamine (DPPE), distearoyl phosphatidyl-ethanolamine (DSPE), dioleylphosphatidyl-ethanolamine (DOPE), diarachidoylphosphatidylethanolamine (DAPE), dilinoleylphosphatidyl-ethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingo-myelin (DS SP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoyl-phosphatidylinositol (DSPI), and dioleoyl-phosphatidylinositol (DOPI).

The term "phospholipid" further includes modified phospholipids, e.g. phospholipids where the hydrophilic group is in turn bound to another hydrophilic group. Examples of modified phospholipids include phosphatidylethanolamines modified with polyethylene glycol (PEG), i.e. phosphatidylethanolamines where the hydrophilic ethanolamine moiety is linked to a PEG molecule of variable molecular weight (e.g. from 300 to 5000 daltons).

Mixtures of phospholipids can also be used, such as, for instance, mixtures of DPPC, DSPC and/or DAPC with DSPS, DPPS, DSPA, DPPA, DSPG, DPPG, Ethyl-DSPC and/or Ethyl-DPPC. Any such combination may further benefit by addition of cholesterol.

Cationic lipids contain positively charged functional groups under physiological conditions. Cationic lipids include, but are not limited to, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N-[1-(2,3,-ditetradecyloxy)propyl]-N,N-dimethyl-N-hydroxyethylammonium bromide (DMRIE), N-[1-(2,3,dioleyloxy)propyl]-N,N-dimethyl-N-hydroxy ethylammonium bromide (DORIE), 3β-[N-(N', N'-dimethylaminoethane) carbamoyl] cholesterol (DC-Chol), dimethyldioctadecylammonium (DDAB) and N,N-dimethyl-2,3-dioleyloxy)propylamine (DODMA).

Examples of phospholipids bearing an overall negative charge are derivatives, in particular fatty acid di-ester derivatives, of phosphatidylserine, such as DMPS, DPPS, DSPS; of phosphatidic acid, such as DMPA, DPPA, DSPA; of phosphatidylglycerol such as DMPG, DPPG and DSPG or of phosphatidylinositol, such as DMPI, DPPI or DPPI. Also modified phospholipids, in particular PEG-modified phosphatidylethanolamines, such as DMPE-PEG2000, DMPE-PEG3000, DMPE-PEG4000, DPPE-PEG5000, DPPE-PEG2000, DPPE-PEG3000, DPPE-PEG4000, DPPE-PEG5000, DSPE-PEG2000, DSPE-PEG3000, DSPE-PEG4000, DSPE-PEG5000, DAPE-PEG2000, DAPE-PEG3000, DAPE-PEG4000 or DAPE-PEG5000 can be used as negatively charged molecules. In some embodiments, the negatively charged compound is selected among DPPA, DPPS, DSPG, DSPE-PEG2000, DSPE-PEG5000 or mixtures thereof.

In some embodiments, the nanoparticle system is a liposome, which includes within its meaning spherical amphiphilic compounds, including lipid compounds, typically in the form of one or more concentric layers. Liposomes are typically formed in aqueous suspensions and contain at least one bilayer of an amphiphilic compound. The liposomes disclosed herein encompass both unilamellar and multilamellar vesicles. In some embodiments, the hydrophilic heads of the amphiphilic compounds forming the external layer of the bilayer are directed towards the exterior of the spherical structure, while the hydrophilic heads of the amphiphilic compounds forming the internal layer of the bilayer are directed towards the interior of the spherical structure. When an agent is encapsulated in a liposome, it is positioned within the hollow sphere of the liposome instead of being within the lipid bilayer or at the surface of the liposome.

The liquid portion of the aqueous phase encapsulated by the inner compartment of the spherical structure of the liposomes is in general the same as the aqueous suspension. In some embodiments, the aqueous phase fills the internal volume of liposomes for the substantial totality of the volume, for example, by more than 90%, preferably more than 95% and typically for about 100%. In some embodiments, the liposome encapsulates a hydrophilic drug in the aqueous phase. In some embodiments, the hydrophilic drug is a platinum agent such as cisplatin or carboplatin.

In some embodiments, the nanocarrier system contains a second group of PEGs which is attached to an anchor lipid at one terminus but does not attach to the ligand at the opposite terminus. The presence of this second group of PEGs allows for modification of pharmaceutical properties of the nanocarrier. In some embodiments, the ratio between the first group of PEGs and the second group of PEGs is about 1:5, about 1:4, about 1:2, about 1:1, about 2:1, about 3:1, about 4:1 or about 5:1. In some embodiments, the second group of PEGs has a molecular weight ranging from about 500 to about 10,000 daltons, from about 1000 to about 8,000 daltons, from about 2000 to about 6,000 daltons, from about 1000 to about 4000 daltons, from about 1000 to about 3000 daltons, from about 1500 to about 2500 daltons, or from about 1800 to about 2200 daltons.

Targeting receptors overexpressed in cancer cells can enhance the cellular uptake of siRNA and anticancer drug by switching from "simple" endocytosis to receptor mediated endocytosis. For instance, Luteinizing Hormone-Releasing Hormone (a synthetic analog of natural LHRH) has been experimentally confirmed to effectively target NLC-siRNA-TAX system to lung cancer cells and substantially increase the anticancer efficacy of the drug. Data obtained in the present competitive inhibition of cytotoxicity by the LHRH receptor ligand confirm the involvement of LHRH receptors in the internalization of LHRH-targeted nanoparticles and the importance of receptor-mediated endocytosis for cellular internalization of such nanoparticles. Nonlimiting example peptide ligands include a full peptide or a peptide comprising a fragment selected from (Gln-His-Trp-Ser-Tyr-DLys (D-Cys)-Leu-Arg-Pro), Arginine-Glycine-Aspartic Acid (RGD), Somatostatin (Cyclic fCYwKVCW-NH2, Bombesin (**QWAVGHL-Ψ(CH2-NH)-L-NH2 (SEQ ID NO: 10)), Angiopep-2 (TFFYGGSRGKRNNFKTEEY (SEQ ID NO: 11)), GlpHWSYKLRPG-NH2, Ac-D-Nal(2)-f(4Cl)-D-Pal(3)-SYkLRPa-NH, QHWSYkLRP-NH-Et, RGD4C (CDCRGDCFC (SEQ ID NO: 12)), c(RGDfK), Celingitide (cyclic-N-Me-VRGDf-NH), Nonlimiting examples of other ligands targeting cancer cells include folate, transferrin, aptamers, antibodies, integrins, and lectins.

Additional exemplary targeting moieties include peptide hormones such as bombesin, stomatostatin and analogs thereof. Cell-surface receptors for peptide hormones have been shown to be overexpressed in tumor cells (Schally (1994) Anti-Cancer Drugs 5:115-130; Lamharzi, et al. (1998) Int. J. Oncol. 12:671-675) and the ligands to these receptors are known tumor cell targeting agents (Grundker, et al. (2002) Am. J. Obstet. Gynecol. 187(3):528-37; Kalmouni, et al. (2019) Cell Mol Life Sci, 76, 2171-2183; WO 97/19954). Carbohydrates such as dextran having branched galactose units (Ohya, et al. (2001) Biomacromolecules 2(3):927-33), lectins (Woodley (2000) J. Drug Target. 7(5): 325-33), and neoglycoconjugates such as Fucalphal-2Gal (Galanina, et al. (1998) Int. J. Cancer 76(1):136-40) can also be used as targeting moieties to treat, for example, colon cancer. It is further contemplated that an antibody or antibody fragment which binds to a protein or receptor, which is specific to a tumor cell, can be used to as a cell-surface targeting moiety. In particular embodiments, the antibody fragment retains at least a significant portion of the full-length antibody's specific binding ability. Examples of antibody fragments include, but are not limited to, Fab, Fab', F(ab')2, scFv, Fv, dsFv diabody, or Fd fragments. Exemplary antibody targeting moieties include bispecific monoclonal antibodies composed of an anti-histamine-succinyl-glycine Fab' covalently coupled with an Fab' of either an anticarcinoembryonic antigen or an anticolon-specific antigen-p antibody (Sharkey, et al. (2003) Cancer Res. 63(2):354-63).

Further examples of targeting ligands include the following:

```
TAT -
                                            (SEQ ID NO: 13)
GRKKRRQRRRPPQ;

pAntp(Penetratin) -
                                            (SEQ ID NO: 14)
RQIKIWFQNRRMKWKK;

pHLIP -
                                            (SEQ ID NO: 15)
AEQNPIYWARYADWLFTTPLLLLDLALLVDADEGT;

ATRAM -
                                            (SEQ ID NO: 16)
GLAGLAGLLGLEGLLGLPLGLLEGLWLGLELEGN;

ACPP -
                                            (SEQ ID NO: 17)
DGGDGGDGGDGPLGLAG-RRRRRRRRC;

pHK-PAS -
                                            (SEQ ID NO: 18)
MIASHLLAYFFTELNGKPILFF
```

Method of Treatment

An aspect of the patent document discloses a method of treating cancer in a subject. The method includes administering to the subject a nanocarrier containing a therapeutically effective amount of one or more bioactive agents, which include for example the siRNAs and anti-cancer agents. In some embodiments, the nanocarriers are sprayed in aerosol form to the subject in need thereof. In some embodiments, the method includes having the subject inhale the nanocarrier system.

In some embodiments, the cancer is oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer. In some embodiments, the cancer is small cell lung cancer. In some embodiments, the cancer is non-small cell lung cancer.

In some embodiments, the subject is determined to have an activating EGFR mutation or an EGFR-TKI-sensitizing mutation at exon 18, exon 19, exon 20 or exon 21. Non-limiting examples of the mutation include a point mutation in the EGFR exon 21 (substituting an arginine for a leucine (L858R)), in-frame deletions (encompassing 4 amino acid residues 750 LREA motif (SEQ ID NO: 19)) of the EGFR exon 19, G719X point mutation(encoded by exon 18), and L861Q point mutation (exon 21).

In some embodiments, the patient or the subject has been treated with one, two, three or more lines of therapy before the treatment with the nanocarrier system disclosed herein. Nonlimiting examples of prior therapy or treatment include stereotactic body radiotherapy, chemotherapy, radiation therapy, and drug therapy.

In some embodiments, the method further comprises administering an additional anti-cancer therapy. In some aspects, the anti-cancer therapy is chemotherapy, radiotherapy, gene therapy, surgery, hormonal therapy, anti-angiogenic therapy or immunotherapy.

One, two, three or more agents for treatment of cancers can be administered as a combination therapy with the nanocarrier system disclosed herein. Non-limiting examples include agents that target cells with alk gene changes (e.g.crizotinib (xalkori),ceritinib (zykadia),alectinib (alecensa),brigatinib (alunbrig),lorlatinib (lorbrena)), drugs that target cells with ros1 gene changes (e.g. crizotinib (xalkori), ceritinib (zykadia), lorlatinib (lorbrena),entrectinib (rozlytrek)), drugs that target cells with braf gene changes (e.g. dabrafenib (tafinlar), trametinib (mekinist)), drugs that target cells with ret gene changes (e.g. selpercatinib (retevmo)), drugs that target cells with met gene changes (e.g. capmatinib (tabrecta)), drugs that target cells with ntrk gene changes as well as angiogenesis inhibitors (e.g. bevacizumab (avastin), ramucirumab (cyramza)). EGFR inhibitors include for example agents used in nscic with egfr gene mutations (e.g. erlotinib (tarceva), afatinib (gilotrif),gefitinib (iressa),osimertinib (tagrisso),dacomitinib (vizimpro)), agents targeting cells with the t790m mutation (e.g. osimertinib (tagrisso)), agents used for squamous cell nsclc (e.g. necitumumab (portrazza)). Non-limiting examples of HER2-targeted drugs include trastuzumab, pertuzumab, lapatinib, neratinib, SYD985 and trastuzumab emtansine (T-DM1), and antibody-drug conjugate thereof (e.g. Trastuzumab duocarmazine). Non-limiting examples of checkpoint inhibitors include those that target PD-1, PD-L1, CTLA4 and TIGIT (T cell immunoglobulin and ITIM domain). Further examples include Ipilimumab (Yervoy®; blocking a checkpoint protein called CTLA-4); pembrolizumab (Keytruda®), Cemiplimab (Libtayo) and nivolumab (Opdivo®) (targeting another checkpoint protein called PD-1); atezolizumab (Tecentriq®), Avelumab (Bavencio), and Durvalumab (Imfinzi) (targeting PD-L1); MK-7684, Etigilimab/OMP-313 M32, Tiragolumab/MTIG7192A/RG-6058, BMS-986207, AB-154 and ASP-8374 (targeting TIGIT), and V-domain Ig suppressor of T cell activation (VISTA). Non-limiting examples of tyrosine kinase inhibitors as chemotherapy include erlotinib, gefitinib, afatinib, dacomitinib and osimertinib.

In some embodiments, the drugs for treating cancers are selected from taxol, cytochalasin B, gramicidin D, ethidium bromide, emetine, mitomycin, etoposide, tenoposide, vincristine, vinblastine, camptothecin (CPT), colchicin, doxorubicin, daunorubicin, mitoxantrone, mithramycin, actinomycin D, 1-dehydrotestosterone, glucocorti-coids, procaine, tetracaine, lidocaine, propranolol, puromycin, methotrexate, 6-mercaptopurine, 6-thioguanine, cytarabine, 5-fluorouracil, decarbazine, mechlorethamine, thiotepa, chlorambucil, melphalan, carmustine (BCNU), lomustine (CCNU), cyclophosphamide, busulfan, dibromo-mannitol, streptozotocin, mitomycin C, cis-dichlorodiamine platinum (II) (DDP), cisplatin, dactinomycin, bleomycin, mithramycin, anthramycin (AMC), exisulind, 2-methoxyestradiol, bortezomib and combinations thereof. In some embodiments, the anticancer agent is cisplatin or carboplatin.

Optional additional ingredients include anti-histaminic agents, anti-inflammatory agents, corticosteroids, nucleic acids, peptides, proteins, oligonucleotides, enzyme imaging agents, cyclo-oxygenase inhibitor, fluorescent dyes and combinations thereof. Preferably, lipid-soluble ingredients are contained within the lipid membrane and water-soluble ingredients are contained within the inner compartment dissolved or dispersed in an aqueous phase contained therein.

The anticancer agents disclosed above can also be administered prior to, subsequent to, or simultaneous with the nanocarrier system of this patent document. The additional agent to the therapy of the nanocarrier system can be administered via any suitable manner, including for example, injection, subcutaneously, inhalation, and oral administration. In some embodiments, one or more the agents disclosed above are encapsulated in the lipid-based nanocarriers (e.g. liposome) of this patent document.

The nanocarrier system and kit disclosed herein enable targeted delivery and treatment and provide a favorable organ distribution and superior anticancer effect when compared with treatment by a single drug, inhibitor of one EGFR-TK and non-targeted therapy. For example, the ratio of drug distribution by the nanocarrier system in an intended organ over other organs can reach at least 8:1, at least 9:1, at least 10:1, at least 12:1, at least 14:1, at least 16:1, at least 18:1, at least 20:1, at least 25:1, at least 30:1, at least 40:1, at least 50:1, at least 60:1, at least 70:1, at least 80:1, at least 90:1, at least 100:1, at least 120:1, at least 140:1, at least 160:1, at least 180:1, at least 200:1, at least 250:1, at least 300:1, at least 350:1, at least 400:1, at least 500:1, or at least 600:1. In some embodiments, the intended organ is lung and the drug distribution is selective in lung over other organs including one or more or all of brain, heart, spleen, kidney, and liver. In some embodiments, the intended organ is lung and the drug distribution is selective in lung over liver in a ratio by at least 9:1, at least at least 10:1, at least 12:1, at least 14:1, at least 16:1, at least 18:1, at least 20:1, at least 25:1, or at least 30:1.

Accordingly, this patent document provides a method of selectively distributing one or more therapeutic agents in an organ of a subject. The method includes administering to the subject a nanocarrier system disclosed herein. In some embodiments, the nanocarrier system is sprayed in aerosol form to the subject in need thereof. In some embodiments, the method includes having the subject inhale the nanocarrier system.

Kit and Pharmaceutical Composition

A related aspect of the patent document provides a kit or pharmaceutical composition incorporating the nanocarrier disclosed herein. In some embodiments, the kit is a sprayer or a nebulizer. In some embodiments, the kit includes one or more drugs disclosed above as a secondary agent used in combination with nanocarrier system of this patent document.

The nanocarrier system disclosed herein or its composition can be formulated for inhalation according to procedures known in the literature, including for example U.S. Pat. Nos. 9,445,993, 9,603,906; 8,912,193, the entire disclosure of which is incorporated herein by reference. The formulation can be in any suitable form for inhalation including for example liquid or dry powder formulations.

The pharmaceutical composition of the nanocarrier system for the methods or kit describe above generally includes one or more pharmaceutically acceptable carriers. Nonlimiting examples of carriers include physiologically acceptable surface active agents, glidants, plasticizers, diluents, excipients, smoothing agents, suspension agents, film forming substances, and coating assistants. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents. Suitable exemplary binders include crystalline cellulose, sucrose, D-mannitol, dextrin, hydroxypropylcellulose, hydroxypropylmethylcellulose, polyvinylpyrrolidone, and the like. Suitable exemplary disintegrants include starch, carboxymethylcellulose, calcium carboxymethylcellulose, croscarmellose sodium, sodium carboxymethylstarch, and the like. Suitable exemplary solvents or dispersion media include water, alcohol (for example, ethanol), polyol (for example, glycerol, propylene glycol, and polyethylene glycol, sesame oil, corn oil, and the like), and suitable mixtures thereof that are physiologically compatible. Suitable exemplary solubilizing agents include polyethylene glycol, propylene glycol, D-mannitol, benzylbenzoate, ethanol, trisaminomethane, cholesterol, triethanolamine, sodium carbonate, sodium citrate, and the like. Suitable exemplary suspending agents include surfactants such as stearyltriethanolamine, sodium laurylsulfate, laurylaminopropionic acid, lecithin, benzalkonium chloride, benzethonium chloride, glycerin monostearate, coconut oil, olive oil, sesame oil, peanut oil, soya and the like; and hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose, and the like. Suitable exemplary isotonic agent includes sodium chloride, glycerin, D-mannose, and the like. Suitable exemplary buffer agents include buffer solutions of salts, such as phosphate, acetates, carbonates, and citrates. Suitable exemplary soothing agents include benzyl alcohol, and the like. Suitable exemplary antiseptic substances include para-oxybenzoic acid esters, chlorobutanol, benzyl alcohol, phenethyl alcohol, dehydroacetic acid, sorbic acid, and the like. Suitable exemplary antioxidants include sulfite salts, ascorbic acid, and the like. Suitable exemplary sealers include, but are not limited to HPMC (or hypromellose), HPC, PEG and combinations thereof. Suitable exemplary lubricants include magnesium stearate, calcium stearate, talc, colloidal silica, hardened oil and the like.

In further exemplary embodiments for solid preparations, carriers or excipients include diluents, lubricants, binders, and disintegrants. In exemplary embodiments for liquid preparations, carriers include solvents, solubilizing agents, suspending agents, isotonic agents, buffer agents, soothing agents, and the like. Acceptable additional carriers or diluents for therapeutic use and the general procedures for the preparation of pharmaceutical compositions are well known in the pharmaceutical art, and are described, for example, in Remington's Pharmaceutical Sciences, 18th Ed., Mack Publishing Co., Easton, PA (1990), which is incorporated herein by reference in its entirety.

Administration Regimen

The nanocarrier of this patent document may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; or (c) administration via injection, subcutaneously, intraperitoneally, intravenously, intramuscularly, intradermally, intraorbitally, intracapsularly, intraspinally, intrasternally, or the like, including infusion pump delivery. In some embodiments, the nanocarrier is administered via intranasal spray. A preferred method of delivery specifically to the lungs for treatment of lung tumor is inhalation of nanoparticles. Such local inhalation delivery enhances antitumor activity and limits adverse side effects on healthy organs.

The therapeutically effective amount of the nanocarrier or its bioactive agents will depend on the route of administration, the type of subject, including human, being treated, and the physical characteristics of the specific subject under consideration. The dose can be tailored to achieve a desired effect, but will depend on such factors as weight, diet, concurrent medication and other factors which those skilled in the medical arts will recognize. More specifically, a therapeutically effective amount means an amount effective to prevent, alleviate or ameliorate symptoms of disease or prolong the survival of the subject being treated. Determination of a therapeutically effective amount is well within the capability of those skilled in the art, especially in light of the detailed disclosure provided herein.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of an active ingredient, preferably about 1 mg to about 500 mg, e.g. 5 to 200 mg. In cases of administration of a pharmaceutically acceptable salt, dosages may be calculated as the free acid. In some embodiments, the nanocarrier system or composition is administered 1 to 4 times per day. In some embodiments, the nanocarrier system is administer via inhalation by a subject in need thereof.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body

EXAMPLES

Example 1

Materials for synthesis. Precirol ATO 5 was generously provided by Gattefossé USA (Paramus, NJ). Soybean phosphatidylcholine (SPC), Paclitaxel (TAX), Squalene, Tween-80, Mannitol were purchased from Sigma Aldrich (St. Louis, MO). DSPE-PEG (1,2-distearoyl-sn-glycero-3-phosphoethanolamine-N-[amino(polyethylene glycol)-2000] were obtained from Avanti Polar Lipids (Alabaster, AL). XenoLight DiR obtained from Perkin Elmer (Akron, OH). A modified synthetic analog of Luteinizing Hormone-Releasing Hormone (LHRH) decapeptide (Gln-His-Trp-Ser-Tyr-DLys(D-Cys)-Leu-Arg-Pro) was synthesized according to our design by American Peptide Company, Inc. (Sunnyvale, CA). The sequence of native LHRH peptide, which is similar in human, mouse, and rat, was modified to provide a reactive amino group only on the side chain of a lysine residue, which replaced Gly at the position 6 to yield the superactive, degradation-resistant-Lys-6-des-Gly-10-Pro-9-ethylamide LHRH analog. The synthesized sequence of LHRH peptide is highly efficient for targeting of drug delivery systems specifically to the cancer tumors and Cys residue do not influence the recognition process. The remaining materials were obtained from Sigma Aldrich (St. Louis, MO).

Synthesis of Targeted Drug and siRNA Delivery System. Nanostructured Lipid Carriers (NLC) were developed by nanostructuring the lipid matrix in order to give more flexibility for modulation of drug release, increasing the drug loading and preventing its leakage. This was accomplished by mixing solid lipids with liquid lipids, which resulted in a less ordered lipid matrix with many imperfections that help to accommodate a higher amount of payload. The synthetic procedures were developed to construct cationic NLC, incorporate TAX, and form complexes with anionic siRNAs. Besides the procedures disclosed herein, other methods for nanoparticles reported in literature can also be applied or modified to prepare the nanocarrier system of this patent document. An example of lipid-based nanoparticle preparation is described in U.S. Pat. No. 9,445,993, the entire disclosure of which is incorporated herein by reference.

Drug Containing NLC. NLC were prepared by a modified melted ultrasonic method (J Control Release. 2013; 171: 349-57). The lipid and aqueous phases were prepared separately in glass vials. Typically, the lipid phase consisted of 100 mg Precirol ATO 5 (solid lipid), 100 mg Squalene (liquid lipid) and 5 mg soybean phosphatidylcholine (lipophilic emulsifier). In the preliminary studies to test the design strategy, Paclitaxel (TAX) was used as a model drug to be encapsulated into NLC. To prepare drug-loaded NLC, 5 mg of TAX dissolved in 500 µL of DMSO were added to the hot lipid phase under stirring. Aqueous phase was prepared by dissolving 250 mg Tween-80 (surfactant) and 25 mg DOTAP (cationic lipid) in 10 mL of DI water. In order to prepare PEG coated NLC, 10 mg DSPE-PEG2000 with or without the LHRH peptide were additionally added to the aqueous phase. The data showed that PEG2000 is the most suitable for the linkage of LHRH peptide to the lipid nanoparticles in terms the efficiency of cellular penetration and overall therapeutic effect. XenoLight DIR-labeled NLC was prepared with the addition of XenoLight DIR dye (Perkin Elmer, Akron, OH) into the mixture of lipids as described in literature. Both phases were maintained for 15 min at a temperature above the melting point of the lipid (80° C.) in an oil bath under magnetic stirring (1,000 rpm). The hot lipid phase then was added slowly to the aqueous solution under same temperature and magnetic stirring conditions (1,000 rpm, 80° C.). The melted lipid mass was dispersed in the aqueous solution using a high-speed homogenizer (PRO200, PRO Scientific, Inc.) at 18,000 rpm for 10 min to form a hot O/W emulsion. The crude emulsion was then treated by ultrasonication (TELSONIC, 60 W output) for 5 min at 80° C. The hot emulsion was cooled at 4° C., maintaining the mechanical stirring at 1,000 rpm for 1 h. Finally, the NLC were purified by extensive dialysis against water (10,000 MWCO). Dialyzed nanoparticles (100-150 nm) were collected and subjected to lyophilization using mannitol as lyoprotectant.

Preparation of siRNA-NLC Complexes. The pool of siRNAs, siGENOME Human EGFR (1956) siRNA-SMARTpool (Cat.No M-003114-03-0050, Dharmacon, Lafayette, CO) containing four or more EGFR-specific siRNA duplexes was used to suppress all four EGFRs and limit uncontrolled proliferation of cancer cells, vascular invasion, resistance, and metastases. In some experiments, DY-547 (siGLO Red) labeled siRNA (Ambion, Inc, Austin, TX) replaced pool of siRNAs to visualize siRNA delivered into the cells by a fluorescence or confocal microscope as well as in vivo imaging. According to the validated protocol, siRNA solution was added to the purified nanoparticles dissolved in water to obtain final nucleic acid concentration of 1 µM. The mixture was gently vortexed and incubated at 25° C. for 30 min to ensure complete siRNA binding to NLS. In order to study a siRNA complexation, 1 µM siRNA was added to 10 µg, 20 µg, 30 µg, 40 µg, 50 µg, and 80 µg of cationic NLC. The mixture of NLC and siRNA was vortexed and incubated at room temperature for 30-60 min to allow siRNA to form complexes with the NLC. Next, the amount of free siRNA was visualized by a submarine gel electrophoresis with one well representing 1 µM free siRNA and the rest of the wells representing the above mentioned complexes. The gel was imaged using a Gel Logic 440 Imaging System (Kodak, Rochester, NY).

Characterization of Drug and siRNA Delivery System. Nanoparticle size, shape, charge and loading efficiency were analyzed using Atomic Force Microscopy (AFM, Nanoscope IIIA, Veeco Digital Instruments, Ford, PA), Malvern ZetaSizer Nanoseries (Malvern Instruments, UK), and HPLC (Waters Corporation, Milford, MA).

siRNA Serum Stability. Serum stability of both free siRNA and modified siRNA complexes before and after nebulization was investigated by incubating each formulation at 37° C. with equal volume of human serum to give 50% serum concentration. At each predetermined time interval, (0, 5, 15, 30 min, 1, 2, 3, 4, 5, 6, 7, 24 and 48 h) 50 µL of the mixture were removed and stored at −20° C. until gel electrophoresis was performed. In order to release siRNA from the complexes for gel electrophoresis, each sample was treated with 25 mM of reduced glutathione and 100 µM of PMAA. The aliquots from different incubation time periods were loaded onto 4% NuSieve 3:1 Reliant agarose gels in 1×TBE buffer (0.089 M Tris/Borate, 0.002 M EDTA, pH 8.3; Research Organic Inc., Cleveland, OH) and subjected to submarine electrophoresis. The gels were stained with EtBr, digitally photographed, and scanned using Gel Documentation System 920 (NucleoTech, San Mateo, CA).

Cellular Internalization. In order to visualize a drug, TAX, Oregon Green™ 488 Conjugate (Catalog number: P22310, Grand Island, NY) was used to prepare an aliquot of drug-loaded NLC. Different components of delivery system were labeled with different fluorescent dyes: NLC—near-infrared fluorescence, TAX—green fluorescence and siRNA—red fluorescence, were prepared as described above. A549 adenocarcinomic human basal epithelial (alveolar type II pneumocytes) non-small cell lung cancer (NSCLC) cells were plated in 6 well plates and treated with the fluorescently labelled NLC-TAX-siRNA formulations for three hours. The cells were then visualized using a confocal microscope Leica G-STED SP8 (Olympus America Inc., Melville, NY).

Cytotoxicity, Apoptosis Induction and Immune Response. The toxicities of the developed formulations were compared with a commercially used EGFR inhibitor gefitinib in three types of human lung cancer cells with different resistance to the drug. The following types of NSCLC cell lines were used: (1) NCI-H1781 gefitinib-insensitive (EGFR2-mutant); (2) A549 (no EGFR-TK mutations) with moderate sensitivity to gefitinib; and (3) NCI-H3255 gefitinib sensitive (EGFR1-L858R mutant). Cytotoxicity and apoptosis induction were analyzed by a modified 3-(4,5-Dimethylthiazol-2-yl)-2,5-diphenyltetrazolium bromide (MTT) assay and cell death detection ELISA Plus kit (Roche, Nutley, NJ), respectively. The cells were seeded on a 96 well plate at 10,000 cells per well with 100 µl of growth media in each well and placed in the incubator for 24 hours. After 24 hours, the media was removed and the cells were treated with varying concentrations of above indicated substances. The concentrations of tested substances were prepared using a serial dilution (1:2) to make 12 different working solutions for the cytotoxicity measurement.

For apoptosis induction study, cells were incubated for 72 h with 1 µM of gefitinib (the most effective concentration) or 0.3 ng/ml of NLC-siRNAs-TAX ($IC_{50}$ dose for A549 cells determined by cellular cytotoxicity experiments). The control cells were incubated with fresh media. Previously validated in our laboratory MTT and apoptosis induction measurement protocols were used. In order to test a toxicity of NLC, apoptosis induction was measured in different organs (liver, kidney, spleen, heart, lung, brain) of mice after injection of saline (control) and NLC intravenously or by inhalation.

In order to examine an immune response for the developed complex system, human peripheral blood lymphocytes (PBL) were incubated with non-targeted and targeted NLC containing siRNA within 8 days and concentration of immunoglobulin G (IgG) was measured using immunoperoxidase assay (Immunology Consultants Laboratory, Inc., Newberg, OR).

Expression of EGFR mRNA. Mouse lungs were extracted, trachea and mainstream bronchi were separated, lungs were frozen and homogenized as described. RNA was isolated using RNeasy kit (Qiagen, Valencia, CA) according to manufacturer's protocol. First-strand cDNA was synthesized with Ready-To-Go You-Prime First-Strand Beads (Amersham Biosciences, Piscataway, NJ) with 1 µg of total cellular RNA (from 107 cells) and 100 ng of random hexadeoxynucleotide primer (Amersham Biosciences, Piscataway, NJ). Then, the reaction mixture was immediately subjected to Quantitative Reverse Transcription Polymerase Chain Reaction—QRT-PCR (Applied Biosystems, Inc., Foster City, CA) using previously developed and validated sets of EGFR-TK primers Example 2

In Vivo Lung Cancer Model, Imaging and Treatment. All animal experiments were carried out according to the protocol approved by Institutional Animal Care and Use Committee (IACUC). Nude mice were purchased from the approved commercial vendor (Taconic, Germantown, NY). All aspects of the program for procurement, conditioning/quarantine, housing management, veterinary care and disposal of carcasses followed the guidelines set forth in the NIH Guide for the Care and Use of Laboratory Animals. Animals were housed in the AALAC (American Association for Laboratory Animal Science)—accredited animal facility with free access to food and water. Veterinary care was supplied by Rutgers University Lab Animal Services. Orthotopic lung cancer mouse model was created by intratracheal instillation of A549 lung cancer cells as previously described. The progression of tumor growth was monitored using bioluminescent and magnetic resonance (MRI) imaging. Luciferase transfected cancer cells were visualized in live anesthetized animals using in-vivo bioluminescence IVIS system (Xenogen, Alameda, CA). Luciferin (150 mg/kg) was intraperitoneally administered 10-15 minutes before imaging. All imaging procedures were performed at special imaging facilities of the Rutgers University Molecular Imaging Center as previously described. Mice were anesthetized with isoflurane (4% for induction of anesthesia and 1-2% for maintenance) using XGI-8 Gas Anesthesia System (Xenogen, Alameda, CA) for all imaging procedures. MRI was performed using a 1 T M2™ whole body scanner (Aspect Imaging, Shoham, Israel). Images (repetition time 2607 ms, echo time 44 ms) were recorded in Fast Spin Echo sequence. At a spatial resolution of 312 µm, the tumors were coronal imaged in a single section through the mouse body using an image matrix of 256×256, a field of view of 80 $mm^2$, and 4 excitation. Magnetic resonance signal and tumor volume were calculated using VivoQuant 1.21 software (Invicro, Boston, MA).

Organ distribution of NLC was studied as previously described. Briefly, aliquots of NLC were labeled with near-infrared fluorescent XenoLight DiR dye (Perkin Elmer, Akron, OH). A fluorescent dye was dissolved together with lipids in chloroform. Fluorescence of labeled with DiR NLCs were visualized 24 h after the intravenous administration or by inhalation using IVIS imaging system. Visible light and fluorescence images were taken and overlaid using the manufacturer's software to obtain composite images. The distribution of fluorescence in different organs (liver, kidney spleen, heart, brain and lungs) was analyzed using original software developed in our laboratory. Four-six weeks after the instillation of tumor cells, when the tumor in lungs reached a volume of about 40 $mm^3$, mice were treated on days 0, 3, 7, 11, 14, 17, 21, and 24 with free non-bound TAX (intravenous injections), non-targeted NLC-siRNAs (inhalation), non-targeted NLC-TAX (inhalation), non-targeted NLC-siRNAs-TAX (inhalation), tumor targeted LHRH-NLC-siRNAs-TAX (inhalation). In order to deliver NLC-based system by inhalation, a Collison nebulizer (BGI, Inc., Waltham, MA) was connected to four-port nose-only exposure chambers (the chamber was made by CH Technologies, Westwood, NJ according to our design). The uniformity of the nanoparticle size in the inhalation delivery was previously studied in details. We designed the installation and selected regime of inhalation to keep the inhalation dosage controllable and uniform from animal to animal with a minimal damage to the nanoparticles. The solution of NLC was aerosolized at a flow rate of 2 L/min and then diluted by an additional 2 L/min of air. It was found that aerosolization did not significantly change the shape and size of the nanoparticles. It was also shown that the aerosol distribution between the four ports of the chamber was homogenous. The dose of TAX in all drug-containing formulations was 2.5 mg/kg for the single administration. This dose corresponds to the maximum tolerated dose (MTD) of LHRH-NLC-TAX delivered by inhalation. The MTD was estimated in separate experiments based on animal weight change after the instillation of increasing doses of drug formulation as previously described. The dose of siRNA was 170 μg/kg for the single administration. The dose of free non-bound TAX used for intravenous injection was also 2.5 mg/kg. Animal weight was monitored every day during the treatment period. After the treatment, all mice were anesthetized with isoflurane and euthanized. Changes in tumor volume were used as an overall marker for antitumor activity. After sacrificing the animals, lungs and other organs were excised, washed in ice-cold saline and kept frozen.

Statistical Analysis. Data were analyzed using descriptive statistics, single-factor analysis of variance (ANOVA), and presented as mean values±standard deviation (SD) from four to ten independent measurements. Ten animals were used in each experimental group. The comparison among groups was performed by the independent sample student's t-test. The difference between variants was considered significant if $P<0.05$.

Biological Variables. Age, weight, and underlying health condition for all experimental animals were similar in all experimental groups. To increase scientific rigor, we used animals of both sexes in the experiments since lung cancer affects both genders. No statistically significant difference was found between genders and, therefore, the data for both sexes were combined in one data set.

Example 3

Preparation and Characterization of Nanoparticle-Based Delivery System. The synthesized NLC had a distinct spherical shape and average diameter of 111.3±20 nm. Analysis demonstrates a size distribution of a large number of single nanoparticles and their aggregates in the solution measured by dynamic light scattering (DLS) technique. In contrast, the provided AFM image reveals only a tiny portion of nanoparticles from the sample in their dry state deposited on mica surface, and therefore, it may not represent the actual ratio of small to large nanoparticles in the sample. Consequently, the AFM image confirms a spherical shape of the prepared nanoparticles, and the DLS profile demonstrates the average hydrodynamic size and size distribution of nanoparticles in the sample. The measured average zeta-potential of the particles was about +45 mV. TAX loading efficiency of NLC was estimated to be about 98%. According to the gel retardation assay, disappearance of the siRNA band in the agarose gel after its incubation with 40 μg NLC indicating that all siRNA molecules were complexed by NLC, and therefore the loading efficiency of siRNA into NLC-based delivery system was 100% at this siRNA:NLC w/w ratio. The nanoparticles formed complexes with tested siRNA resulting in practically neutral composition of NLC-based delivery system. Binding of the anionic siRNA to the cationic NLC was studied using an agarose gel retardation assay. Disappearance of the siRNA band in the agarose gel after its incubation with various amounts of NLC (10 μg, 20 μg, 30 μg, 40 μg, 50 μg, and 80 μg) confirms that 40 μg NLC is required to complex 1 μM (~0.33 μg) siRNA, which corresponds to weight NLC/weight siRNA ratio=121. The resulting complexes were stable at 4° C. for at least two months and were effectively internalized by cancer cells. The average siRNA loading was about 2.5 nmole/mg of NLC. In order to estimate an immune response to siRNA incorporated in the NLC-based delivery system, human peripheral blood lymphocytes (PBL) were incubated with non-targeted and targeted NLC containing siRNA within 8 days and concentration of immunoglobulin G (IgG) was measured using immunoperoxidase assay. It was found, that both non-targeted and LHRH-targeted NLC loaded with siRNA did not induce an immune response in human PBL. In addition, measurement of apoptosis induction in vivo in different organs (liver, kidney, spleen, heart, lung, brain) of mice treated with NLC administered by intravenous injection and inhalation did not show any signs of toxicity.

siRNA Serum Stability. The stabilization of siRNA in human serum against the nuclease degradation is essential for in vivo siRNA delivery. Therefore, to examine siRNA protection in the engineered siRNA nanoparticles from nuclease degradation, the complexes were incubated in the presence of 50% human serum at 37° C. Gel electrophoresis experiment demonstrated that the degradation of free non-bound naked siRNA was observed 5 min after the incubation, while 1 h after the beginning of the experiment, siRNA was fully digested (FIG. 2E, upper panel). On the other hand, the complexation of siRNA with NLC effectively stabilized siRNA in human serum for the entire duration of the experiment (48 h). Moreover, nebulization of siRNA complexed with NLC did not decrease siRNA stability and prevented its degradation by nucleases.

Cellular Internalization of NLC-siRNA-TAX. Cellular Internalization of NLC, incorporated drug and siRNA was studied in human A549 NSCLC cells using a confocal microscope. Results show representative fluorescence images of the cells incubated with NLC-siRNA-TAX complexes. Labeled NLC emitted near-infrared (visualized by a confocal microscopy as blue color), siRNA—red and paclitaxel green fluorescence. Superimposition of red and blue colors gives pink color; superimposition of blue and green gives cyan color; superimposition of red and green colors gives yellow color; superimposition of red, green and blue colors gives white color. It was found that NLCs as well as their cargo, TAX and siRNA, successfully internalized into the lung cancer cells. Since fluorescence of siRNA and TAX was quenched in complexes, registered red and green fluorescence inside the cells reflected the release and localization of free non-bound siRNA and TAX inside cancer cells, respectively. It was found, that developed NLC-based delivery system effectively transferred siRNA and TAX and released them in cancer cells.

Cytotoxicity and Competitive Inhibition by LHRH peptide. The toxicity studies showed that the nanoparticles without siRNA and drug as well as LHRH peptide alone did not demonstrate any toxicity. The delivery of TAX by non-targeted NLC substantially enhanced cytotoxicity of TAX against cancer cells. Furthermore, it was found that targeting of NLC-TAX using LHRH significantly increased the cytotoxicity of complexes in LHRH-positive lung cancer cells. To confirm that such an enhancement in cytotoxicity of LHRH-NLC-TAX system is associated with its binding to LHRH receptor, NSCLC cells was incubated with different concentrations of LHRH peptide (ligand for LHRH receptor) and then measured cytotoxicity of LHRH-NLC-TAX complex. Data obtained showed that LHRH receptor ligand limited cytotoxicity of LHRH-NLC-TAX in a concentration-dependent manner.

The efficacy of killing lung cancer cells and apoptosis induction by the LHRH-NLC-TAX multifunctional complex system was compared with a traditional clinically used EGFR-TK inhibitor—gefitinib. In these experiments, three types of human lung cancer cells with different sensitivity to gefitinib were incubated for 72 h with the most effective concentration (1 µM) of gefitinib or $IC_{50}$ dose of LHRH-NLC-TAX for A549 cells (0.3 ng/mL). It was found that H1781 cells were most resistant to gefitinib. In contrast, H3255 cells with mutated EGFR1-TK were the most sensitive to gefitinib. A549 NSCLC cells had a moderate sensitivity to gefitinib. The efficiency of apoptosis induction by the conventional drug (gefitinib) and NLC-siRNAs-TAX were compared. It was found that apoptosis induction by gefitinib correlated with its cytotoxicity, while NCL-siRNAs-TAX induced apoptosis with almost the same efficiency ($P>0.05$) in all tested cell lines with differing sensitivity to gefitinib. Overall, NLC-siRNAs-TAX was 3-7 times more efficient when compared with gefitinib. Our data show that the approach utilizing complex gene- and chemotherapy (simultaneous delivery of TAX and siRNAs targeted to the pool of EGFR-TKs) effectively killed all types of human NSCLC cells (with and without mutations of EGFR-TKs).

Example 4

Evaluation of Orthotopic Lung Cancer Model. An orthotopic mouse model of human lung cancer was developed according to a protocol approved by the Institutional IACUC. According to the protocol, NSCLC cancer cells (human A549) transfected with luciferase in a medium containing 5 pµmole of EDTA were administered intratracheally to the mouse lung through a catheter. It was shown that slight disruption of the pulmonary epithelium or the surfactant layer by co-administration of either pancreatic elastase or EDTA allowed significantly better tumor engraftment. Suspension of cancer cells and this concentration of EDTA displayed no adverse side effects in test animals. Rapid growth of lung tumor occurred in 80% of animals. The progression of tumor growth was monitored using bioluminescent (IVIS) and magnetic resonance imaging systems. As an example of MRI image processing, representative images of an entire mouse and mouse lungs with tumor were analyzed. MRI was performed using a 1 T M2™ whole body scanner and images were recorded in Fast Spin Echo sequence. Magnetic resonance signal and tumor volume were calculated using VivoQuant 1.21 software. Image analysis clearly shows the development of lung tumor and validates the orthotopic lung tumor model. Bioluminescence images of transfected NSCLC cells also support the development of lung cancer.

Biodistribution of Tumor Receptor-Targeted and Non-Targeted Delivery Systems. Body distribution of the proposed LHRH-NLC system was studied and compared with those for non-targeted NLC delivered either intravenously or by inhalation. A previously constructed and tested four channel instillation for inhalation delivery of nanoparticle drugs was used in these experiments. The instillation allowed for a uniform distribution of inhaled substances among the four inhalation chambers contained anesthetized animals with a minimal influence on the shape and efficacy of inhaled substances.

The accumulation of fluorescently labelled targeted and non-targeted NLCs within different organs (lungs, liver, kidney, spleen, brain, heart) of mouse containing orthotopic lung tumor was studied using IVIS system in live anesthetized animals and their excised organs. A typical image of an entire animal and its organs treated with targeted and non-targeted NLCs was analyzed, C along with calculated average distribution of tested nanocarriers. It was found that non-targeted NLC after intravenous injection accumulated predominately in the mouse liver and partially in kidney and spleen. Inhalation of such nanoparticles substantially changed their body distribution with a significant decrease in accumulation in the liver and efficient retaining in the lungs. Targeting of the NLCs specifically for tumor cells by the LHRH peptide significantly enhanced accumulation of LHRH-NLC nanoparticles in the lungs with tumor after inhalation delivery. It should be stressed that accumulation of tumor-targeted nanoparticles (LHRH-NLC) after inhalation is greater when compared not only with I.V. administration of these particles but also with non-targeted NLCs also delivered by inhalation. This phenomenon creates prerequisites for enhancing the anticancer activity of delivered biologically active anticancer agents and limit adverse side effects of the treatment.

Efficacy of Inhalation Treatment of Lung Cancer using Nanoparticle-Based Tumor-Targeted Complex Delivery System. Efficient accumulation of siRNAs and a chemotherapeutic drug in the lungs as well as their uptake by cancer cells does not automatically guarantee suppression of targeted mRNAs and corresponding proteins accompanied by effective killing of cancer cells. Consequently, the efficiency of the suppression of all four variants of EGFR-TK receptors, cell death induction in tumor cells and inhibition of tumor growth by the proposed NLC-based delivery system were evaluated. To this end, an expression of the most common variants of EGFR-TKs mRNAs was analyzed. Induction of apoptosis and/or necrosis was also studied in the same experimental setting. The correlation between the expression of studied proteins, degree of apoptosis and/or necrosis, and tumor suppression by the LHRH-NLC-siRNA-TAX with appropriate controls were analyzed. It was shown that targeted delivery of siRNA pool specifically to lung tumor cells effectively suppressed all four major forms of EGFR-TK receptors. Measurement of tumor volume at the end of the experiment showed that treatment of mice with TAX delivered intravenously decreased the lung tumor just in 1.1 times, treatment of mice by inhalation with NLC-siRNA shrank the tumor in 1.3 times, NLC-TAX—in 1.9 times, while the combination of NLC with siRNA and TAX decreased the tumor size in 5.6 times. It should be stressed that the combination of siRNA and TAX delivered together by inhalation using NLC shrank the volume of lung tumor significantly better when compared with either the drug or siRNA alone. It was found that lung tumor was almost completely eliminated after the treatment of mice with tumor targeted LHRH-NLC-siRNAs-TAX delivered by inhalation. Finally, it was found that simultaneous targeted inhalation delivery of siRNAs with TAX (a combination of gene- and chemotherapy) resulted in killing of NSCLC cells, limiting and suppression of tumor growth with the efficiency that cannot be achieved when either therapy is applied alone/separately.

Example 5

To select the most appropriate carrier for inhalatory delivery of a drug and siRNA, different nanocarriers (liposomes, micelles, PAMAM and PPI dendrimers, linear polymers, silica, gold and NLC nanoparticles) were screened for inhalation delivery. Preferential accumulation and retention of a carrier, siRNA and drug in the lungs versus other organs after the inhalation delivery were used as criteria for the selection. As a result of the analysis of the data, a lipid-based system was selected as the best carriers for inhalation co-delivery of nucleic acids and drugs. Drug-contained positively charged NLC were prepared in order to make complexes with negatively charged siRNAs.

Paclitaxel (TAX) was selected as a model lipophilic anticancer drug that can be easily encapsulated in the lipids of NLC. In addition, this drug has been used in the clinic alone or in combination with platinum-based chemotherapeutic agents for treatment of advanced NSCLC. A Pool of siRNAs targeted to different TKs was selected to inhibit all four types of EGFRs in NSCLC cells. It was found that the high specificity of RNA interference mechanisms and suppression of all four types of EGFRs improved anticancer efficiency of the proposed delivery system and provided a synergetic effect with the anticancer drug. In addition, the pool of siRNAs potentially can expand the range of therapy-responsive NSCLC patients when compared with currently used EGFR-targeted treatment options.

Example 6

Inhalation treatment of mice with orthotopic model of human lung cancer by liposomal cisplatin or liposomal carboplatin.

Egg phosphatidylcholin (EPC), Cholesterol (Chol), and 1,2,-distearoyl-sn-glycero-3-phosphoethanolamine-N-aminopolyethelenglycol-Mw-2000 ammonium salt (DSPE-PEG) were purchased from Avanti Polar Lipids (Alabaster, AL); cisplatin (Cis) and carboplatin (Carb) were purchased from Sigma (St. Louis, MO).

PEGylated "neutral" liposomes (Lip) were prepared using lipids (EPC, Cholesterol, and DSPE-PEG in ratio 51:44:5, respectively). For liposomal carboplatin (Lip-Carb) preparation, lipids: EPC, Cholesterol and 1,2,-distearoyl-sn-glycero-3-phosphoethanolamine-N-aminopolyethelenglycol-Mw-2000 ammonium salt (DSPE-PEG) and Carboplatin were dissolved in Chloroform, evaporated to a thin film layer using rotary evaporator Rotavapor® R-210/R-215 (BUCHI Corp., New Castle, DE, USA) and rehydrated with 0.9% NaCl or any other appropriate buffer to final lipid concentration 20 mM. Carboplatin concentration was 4 mg/ml. Lipids mole ratio for this formulation was 51:44:5 mole % EPC:Chol:DSPE-PEG respectively. Liposome size was decreased using water bath sonication. Free Carboplatin was separated from liposomes by dialyses against 100 volumes of the appropriate during 24 hours.

For liposomal cisplatin (Lip-Cis) preparation, lipids: EPC, Cholesterol and 1,2,-distearoyl-sn-glycero-3-phosphoethanolamine-N-aminopolyethelenglycol-Mw-2000 ammonium salt (DSPE-PEG) were dissolved in in Chloroform, evaporated to a thin film layer using rotary evaporator Rotavapor® R-210/R-215 (BUCHI Corp., New Castle, DE, USA) and rehydrated with 0.9% NaCl or any other appropriate buffer containing 2 mg/ml Cisplatin to final lipid concentration 20 mM. Lipids mole ratio for this formulation was 51:44:5 mole % EPC:Chol:DSPE-PEG respectively. Liposome size was decreased using water bath sonication. Free Cisplatin was separated from liposomes by dialyses against 100 volumes of appropriate buffer during 24 hours.

The aliquots of liposomes were destroyed in isopropanol in a ratio of 10:90 (liposomes:isopropanol) and the concentration of trapped drug was determined by high-performance liquid chromatography using a symmetry C18 column (150 mm×4.6 mm, Waters Corporation, Milford, MA, USA) operated at room temperature. The mobile phase consisted of 0.1% trifluoroacetic acid in water/acetonitrile 25:75 v:v; the flow rate was set to 1.0 ml/min, wavelength 480 nm. The chromatographic instillation consisted of a Model 1525 pump (Waters Corporation, Milford, MA, USA), a Model 717 Plus auto-injector (Waters Corporation) and a Model 2487 variable wavelength UV detector (Waters Corporation) connected to the Millennium software. Loading efficacy of both drugs was about 90% from total amount. Electrical charge of liposomes was measured using ZetaPALS Zeta Potential Analyzer (Brookhaven Instruments, New York, NY). The average zeta potential of empty and loaded PEGylated liposomes was −10±2 mV.

All animal experiments were carried out according to the protocol approved by Institutional Animal Care and Use Committee (IACUC). Nude mice were purchased from the approved commercial vendor (Taconic, Germantown, NY). All aspects of the program for procurement, conditioning/quarantine, housing management, veterinary care and disposal of carcasses followed the guidelines set forth in the NIH Guide for the Care and Use of Laboratory Animals. Animals were housed in the AALAC (American Association for Laboratory Animal Science)—accredited animal facility with free access to food and water. Veterinary care was supplied by Rutgers University Lab Animal Services. Orthotopic lung cancer mouse model was created by intratracheal instillation of human lung cancer cells. The progression of tumor growth was monitored using bioluminescent and magnetic resonance (MRI) imaging. Luciferase transfected cancer cells were visualized in live anesthetized animals using in-vivo bioluminescence IVIS system (Xenogen, Alameda, CA). Luciferin (150 mg/kg) was intraperitoneally administered 10-15 minutes before imaging. All imaging procedures were performed at special imaging facilities of the Rutgers University Molecular Imaging Center as previously described. Mice were anesthetized with isoflurane (4% for induction of anesthesia and 1-2% for maintenance) using XGI-8 Gas Anesthesia System (Xenogen, Alameda, CA) for all imaging procedures. MRI was performed using a 1 T M2™ whole body scanner (Aspect Imaging, Shoham, Israel). Images (repetition time 2607 ms, echo time 44 ms) were recorded in Fast Spin Echo sequence. At a spatial resolution of 312 μm, the tumors were coronal imaged in a single section through the mouse body using an image matrix of 256×256, a field of view of 80 $mm^2$, and 4 excitation. Magnetic resonance signal and tumor volume were calculated using VivoQuant 1.21 software (Invicro, Boston, MA).

Four-six weeks after the instillation of tumor cells, when the tumor in lungs reached a volume of about 40 $mm^3$, mice were treated on days 0, 3, 7, 11, 14, 17, 21, and 24 with empty liposomes delivered by intravenous injection (IV) or inhalation, free non-bound cisplatin (CIS) and carboplatin (Carb) (IV), liposomal form of Cis (Lip-Cis) or Carb (Lip-Carb) delivered intravenously or by inhalation. In order to deliver liposome-based system by inhalation, a Collison nebulizer (BGI, Inc., Waltham, MA) was connected to four-port nose-only exposure chambers (the chamber was made by CH Technologies, Westwood, NJ according to our design). The uniformity of the nanoparticle size in the inhalation delivery was previously studied in details. The installation was designed and regime of inhalation was selected to keep the inhalation dosage controllable and uniform from animal to animal with a minimal damage to the nanoparticles. The solution of NLC was aerosolized at a flow rate of 2 L/min and then diluted by an additional 2 L/min of air. It was found that aerosolization did not significantly change the shape and size of the nanoparticles. It was also shown that the aerosol distribution between the four ports of the chamber was homogenous. The dose of Cis and Carb in all drug-containing formulations was 2.5 mg/kg for the single administration.

Data were analyzed using descriptive statistics, single-factor analysis of variance (ANOVA), and presented as mean values±standard deviation (SD) from four to ten independent measurements. Ten animals were used in each experimental group. The comparison among groups was performed by the independent sample student's t-test. The difference between variants was considered significant if $P<0.05$.

Age, weight, and underlying health condition for all experimental animals were similar in all experimental groups. To increase scientific rigor, we used animals of both sexes in the experiments since lung cancer affects both genders. No statistically significant difference was found between genders and, therefore, the data for both sexes were combined in one data set.

The data obtained showed that empty liposomes did not cause any statistically significant influence on the growth of lung tumor. Free non-bound Cis and Carb injected intravenously slightly slowed the tumor progression. It should be stressed, that free IV Carb demonstrated somewhat higher antitumor activity after intravenous injection probably because of its better aqueous solubility. Delivery the drugs intravenously in their liposomal form significantly decreased the tumor size. However, the most pronounced antitumor effect was achieved in mice with lung tumor by inhalation with liposomal forms of both drugs (Lip-Cis, Lip-Carb). The results did not show statistically significant differences between antitumor effect of liposomal forms of Cis and Carb either after intravenous injection or inhalation.

It will be appreciated by persons skilled in the art that invention described herein are not limited to what has been particularly shown and described. Rather, the scope of the invention is defined by the claims which follow. It should further be understood that the above description is only representative of illustrative examples of embodiments. The description has not attempted to exhaustively enumerate all possible variations. The alternate embodiments may not have been presented for a specific component of a nanocarrier, or a step of the method, and may result from a different combination of described constituents, or that other un-described alternate embodiments may be available for a composition, kit or method, is not to be considered a disclaimer of those alternate embodiments. It will be appreciated that many of those un-described embodiments are within the literal scope of the following claims, and others are equivalent.

The invention claimed is:

1. A nanocarrier system formulated for in vivo delivery of an anticancer agent by inhalation, comprising:
    (a) a lipid nanoparticle comprising a lipid matrix consisting essentially of at least one lipid that is solid at room temperature and at least one lipid that is liquid at room temperature;
    (b) an anticancer agent incorporated in imperfections in the lipid matrix;
    (c) a first group of polyethylene glycols (PEGs) extending from the surface of the nanoparticle, wherein the PEGs each have an inner terminus bonded to an anchor lipid in the nanoparticle and an outer terminus;
    (d) a ligand bonded to the outer terminus of the first group of PEGs, wherein the ligand is specific to receptors overexpressed in cancer cells; and
    (e) one or more siRNAs distributed on the surface of the nanoparticle;
    wherein the lipid nanoparticle is not a liposome.

2. The nanocarrier system of claim 1, wherein the lipid nanoparticle comprises two or more lipids selected from the group consisting of triglycerides, partial glycerides, fatty acids, and steroids and waxes.

3. The nanocarrier system of claim 1, wherein the anticancer agent is selected from the group consisting of cisplatin, carboplatin, paclitaxel, doxorubicin, erlotinib, gefitinib, afatinib, dacomitinib, osimertinib imatinib, PD 153035, picropodophyllin, PP2, staurosporine, and Tyrphostin AG 490.

4. The nanocarrier system of claim 1, wherein the first group of PEGs has a molecular weight ranging from about 1000 to about 3000 daltons.

5. The nanocarrier system of claim 1, wherein the anchor lipid is selected from the group consisting of 1,2-Distearoyl-sn-glycero-3-phosphoethanolamine (DSPE), N-[1-(2,3-Dioleoyloxy)propyl]-N,N,N-trimethylammonium methyl-sulfate (DOTAP), and dioleoylphosphatidylethanolamine (DOPE).

6. The nanocarrier system of claim 1, wherein the ligand is Gln-His-Trp-Ser-Tyr-DLys(D-Cys)-Leu-Arg-Pro.

7. The nanocarrier system of claim 1, further comprising a second group of PEGs extending from the surface of the nanoparticle, wherein the second group of PEGs are not bonded to the ligand.

8. The nanocarrier system of claim 1, wherein the nanoparticle has an average diameter ranging from about 100 to about 300 nm.

9. The nanocarrier system of claim 1, wherein the anticancer agent is cisplatin or carboplatin.

10. The nanocarrier system of claim 1, wherein the siRNAs target one or more of EGFR1, EGFR2, EGFR3, and EGFR4.

11. A kit comprising the nanocarrier system of claim 1.

12. The kit of claim 11, which is a nebulizer.

13. A method of treating cancer comprising administering the nanocarrier system of claim 1 by inhalation.

14. The method of claim 13, wherein the cancer is small cell lung cancer.

15. The method of claim 13, wherein the cancer is non-small cell lung cancer.

16. The method of claim 13, further comprising administering to the subject an additional therapy selected from the group consisting of chemotherapy, radiotherapy, gene therapy, surgery, hormonal therapy, anti-angiogenic therapy and immunotherapy.

17. The method of claim 13, wherein the cancer is resistant to the treatment of a prior tyrosine kinase inhibitor.

* * * * *